(12) United States Patent
Tokuda et al.

(10) Patent No.: US 8,440,619 B2
(45) Date of Patent: May 14, 2013

(54) UTILIZATION OF HYPERTENSION/HYPERCARDIA-PREVENTING EFFECT OF D-ALLOSE

(75) Inventors: Masaaki Tokuda, Kagawa (JP); Shoji Kimura, Kagawa (JP); Ken Izumori, Kagawa (JP)

(73) Assignees: National University Corporation Kagawa University, Takamatsu-shi (JP); Matsutani Chemical Industry Co., Ltd., Itami-shi (JP)

( * ) Notice: Subject to any disclaimer, the term of this patent is extended or adjusted under 35 U.S.C. 154(b) by 664 days.

(21) Appl. No.: 12/065,452

(22) PCT Filed: Aug. 31, 2006

(86) PCT No.: PCT/JP2006/317217
§ 371 (c)(1),
(2), (4) Date: May 7, 2009

(87) PCT Pub. No.: WO2007/026820
PCT Pub. Date: Mar. 8, 2007

(65) Prior Publication Data
US 2009/0305999 A1 Dec. 10, 2009

(30) Foreign Application Priority Data

Aug. 31, 2005 (JP) ................................ 2005-251758

(51) Int. Cl.
*A61K 38/00* (2006.01)
*A61K 9/12* (2006.01)
*A61K 31/70* (2006.01)
*A61P 9/00* (2006.01)

(52) U.S. Cl.
USPC ........................... 514/15.6; 514/15.7; 514/23

(58) Field of Classification Search ................. 514/15.6, 514/15.7, 23
See application file for complete search history.

(56) References Cited

U.S. PATENT DOCUMENTS 3,036,062 A * 5/1962 MacPhillamy et al. ............ 536/5
6,352,975 B1 * 3/2002 Schreiner et al. .............. 514/8.1
2005/0245459 A1 11/2005 Izumori et al.

FOREIGN PATENT DOCUMENTS

JP 2002068970 A * 3/2002
WO 2003/097820 A1 11/2003

OTHER PUBLICATIONS

Sekiya, "Antioxidative function of rare sugar D-psicose, etc.", Nippon Shokuhin Kagaku Kogaku Taikai Koenshu, 2001, p. 107, vol. 48.
Izumori et al., "Production Plan and Manufacturing Possibility of Rage Sugars", Foods and Development, 2003, pp. 66-69, vol. 38, No. 1. (Partial English Translation).
Nishiyama et al., "The SOD Mimetic Tempol Ameliorates Glomerular Injury and Reduces Mitogen-Activated Protein Kinase Activity in Dahl Salt-Sensitive Rats", J. Am. Soc. Nephrol., 2004, p. 306-315, vol. 15.
Fukai, "Oxidant Stress and Hypertension—Role of NAD(P)H oxidase-", Igaku no Ayumi, 2002, pp. 554-564, vol. 202, No. 9. (Partial English Translation).
Kimura et al., D-allose, an all-cis aldo-hexose, suppresses development of salt-induced hypertension in Dahl rats, Journal of Hypertension, Oct. 2005, pp. 1887-1894, vol. 23, No. 10.
Shoji Kimura et al; D-allose, an all-cis aldo-hexose, suppresses development of salt-induced hypertension in Dahl rats; Journal of Hypertension; Oct. 2005; vol. 23; No. 10; pp. 1887-1894, cited ISR.

* cited by examiner

*Primary Examiner* — Patrick T. Lewis
*Assistant Examiner* — Everett White
(74) *Attorney, Agent, or Firm* — Westerman, Hattori, Daniels & Adrian, LLP

(57) ABSTRACT

The object is to provide a novel application of D-allose (e.g., use for prevention of hypertension or hypercardia). Thus, disclosed is a composition for preventing the increase in blood pressure which comprises D-allose as an active ingredient; or a composition containing D-allose and/or a derivative thereof, preferably in an amount of 0.1 to 50% by weight. Preferably, the composition is in a form selected from the group consisting of a food additive, a food material, a beverage/food, a health beverage/food, a pharmaceutical and a feeding stuff which can be used for the prevention and treatment of a cardiovascular system disorder (e.g., hypertension, hypercardia). The increase in blood pressure may be caused by salt-sensitive hypertension. Also disclosed is use of D-allose for preventing the increase in blood pressure (excluding medical practices).

6 Claims, 4 Drawing Sheets

Aorta ring DHE images

UTILIZATION OF HYPERTENSION/HYPERCARDIA-PREVENTING EFFECT OF D-ALLOSE

TECHNICAL FIELD

The present invention relates to a technique for using D-allose in suppressing the onset of hypertension. More specifically, the invention relates to the utilization of the action of D-allose in suppressing the onset of hypertension by allowing D-allose to be ingested or drunk or orally given in forms of food additives, food materials, foods and drinks, health foods and drinks, pharmaceutical agents, and feeds. Additionally, the invention relates to the utilization of the action thereof in suppressing the onset of cardiovascular disorders such as hypercardia as an effect thereof in suppressing the onset of hypertension.

[Descriptions of English Expressions and Abbreviations as Used in the Following Tables and Figures]

Tables 1 and 2, and FIG. 1
DR: salt-resistant Dahl rat
DS: salt-sensitive Dahl rat
Table 3
WKY: Wister Kyoto rat
SHR: spontaneously hypertensive rat
FIGS. 2a and 2b
DR: salt-resistant Dahl rat
DS: salt-sensitive Dahl rat
DHE: dihydroethidium
cpm/mg dry tissue: cpm per 1 mg of dry tissue
FIG. 3
SHR: spontaneously hypertensive rat

BACKGROUND ART

Hypertension is a disease at the highest incidence rate worldwide and domestically. It is suggested that the increase of oxidative stress in biological cardiovascular organs and tissues has a significant role in the progress of hypertension or related diseases such as arteriosclerosis, hypercardia and renal function impairment (Non-patent Document 1, Non-patent Document 2). It was observed in the past that the generation of active oxygen and the like increased during blood pressure elevation and during disorders of cardiovascular organs, such as cardiovascular tubes and renal system, following the increase. It is also suggested that such active oxygen and the like cause hypertensive organ function disorders.

Because hypertensive patients generally never feel sick, the patients frequently never visit doctors until organ impairment begins at the last stage, so that the patients lead their lives without any treatment of the disease. Therefore, hypertension is the main cause of the incidence rate and mortality of cardiovascular diseases in humans. A great number of hypertensive patients are sensitive to salt contents from the standpoint that highly salty diets increase blood pressure or that blood pressure already elevated is exacerbated.

It has been known recently that the administration of a pharmaceutical agent eliminating active oxygen to hypertensive model animals or to humans is effective for suppressing hypertensive organ disorders and additionally for suppressing blood pressure elevation. In salt-sensitive hypertensive model rats where blood pressure is elevated in a manner dependent on the salt intake, the efficacy of such agent eliminating active oxygen is prominently observed (Non-patent Document 3).

Non-patent Document 1: Curr Hypertens Rep 2000; 2: 98-105.
Non-patent Document 2: Curr Hypertens Rep 2002; 4: 160-166.
Non-patent Document 3: J Am Soc Nephrol 2004; 15: 306-315.

DISCLOSURE OF THE INVENTION

Problems to be Solved by the Invention

In accordance with the invention, a novel use of D-allose (a use for suppressing the onset of hypertension) is provided. Currently, lifestyle related diseases such as hypertension have spread in the developed counties mainly including European countries and USA. The finding is also found in Japan with no exception. Rapid increase of lifestyle related diseases following the change of the dietary environment into the European and USA styles has been prominent. Consequently, death cases because of cardiovascular diseases such as hypercardia have been likely increased in recent years.

Meanwhile, pharmaceutical agents having higher therapeutic efficacies for hypertension for clinical practice in the related art have generally serious adverse actions and are furthermore problematic in view of the multiple toxicities from combination therapies with multiple drugs, so these pharmaceutical agents are not suitable for the administration over a long term. The invention has been done so as to overcome such problems in the related art. It is the major object of the invention to provide a pharmaceutical agent and a functional food, which are capable of preventing, ameliorating and therapeutically treating diseases in relation with hypertension without any concerns about adverse actions.

For subjects without any sufficiently efficacious routine pharmaceutical therapies for use in the therapeutic treatment of hypertension, desirably, the pharmaceutical therapies would be improved. Additionally, the increase of these pathologic symptoms indicates the demand for a more innovative therapeutic intervention or strategy, which can be an alternative of the current approach or which can help the approach. So as to cope with such demand in accordance with the invention, it is provided a technique for using D-allose, by which the onset of hypertension and the onset of cardiovascular diseases such as hypercardia can be suppressed, via a simple intake or oral administration of D-allose in forms of food additives, food materials, foods and drinks, health foods and drinks, pharmaceutical products and feeds.

Means for Solving the Problem

The invention is summarized as a composition described below in (1) through (5).

(1) A composition for suppressing the increase of blood pressure, the composition containing D-allose as the active ingredient.
(2) A composition for suppressing the increase of blood pressure, as described above in (1), where the composition is in blend with D-allose and/or a derivative thereof.
(3) A composition for suppressing the increase of blood pressure, as described above in (1) or (2), where D-allose and/or a derivative thereof is blended to a content of 0.1 to 50% by weight in the composition.
(4) A composition for suppressing the increase of blood pressure, as described above in any one of (1) through (3), where the composition is in a form selected from the group consisting of food additives, food materials, foods and drinks, health foods and drinks, pharmaceutical products and feeds in blend with D-allose and/or a derivative thereof as the active ingredient.

(5) A composition for suppressing the increase of blood pressure, as described above in (4), where the composition is in a form selected from the group consisting of food additives, food materials, foods and drinks, health foods and drinks, pharmaceutical products and feeds in blend with D-allose and/or a derivative thereof as the active ingredient, and which can be used for the prevention and therapeutic treatment of the onset of hypertension and/or the onset of cardiovascular diseases such as hypercardia.

(6) A composition for suppressing the increase of blood pressure, as described above in any one of (1) through (5), where the increase of blood pressure is due to salt-sensitive hypertension.

The invention is summarized as a method for using D-allose, as described below in (7) through (11) (excluding the use for clinical practice).

(7) A method for using D-allose for suppressing the increase of blood pressure (excluding the use for clinical practice; the same is true herein below).

(8) A method for using D-allose as described above in (7), where D-allose is D-allose, and/or a derivative thereof, or a composition in blend with D-allose and/or a derivative thereof.

(9) A method for using D-allose as described above in (8), where in case that D-allose is a composition in blend with D-allose and/or a derivative thereof, the composition is in a form selected from the group consisting of food additives, food materials, foods and drinks, health foods and drinks, pharmaceutical products and feeds.

(10) A method for using D-allose as described above in (9), where the composition is in a form selected from the group consisting of food additives, food materials, foods and drinks, health foods and drinks, pharmaceutical products and feeds in blend with D-allose and/or a derivative thereof as the active ingredient, and which can be used for the prevention and therapeutic treatment of the onset of hypertension and/or the onset of cardiovascular diseases such as hypercardia.

(11) A method for using D-allose as described above in (9) or (10), where D-allose and/or a derivative thereof is blended to a content of 0.1 to 50% by weight in the composition.

(12) A method for using D-allose as described above in any one of (7) through (11), where the increase of blood pressure is due to salt-sensitive hypertension.

Advantage of the Invention

The invention can provide the use of D-allose for suppressing the onset of hypertension.

More specifically, the invention can provide the technique for using D-allose, by which the suppression of the onset of hypertension and the suppression of the onset of cardiovascular diseases such as hypercardia as the effect thereof on suppressing the onset of hypertension can be suppressed, via a simple ingestion or oral administration of D-allose in forms of food additives, food materials, foods and drinks, health foods and drinks, pharmaceutical products and feeds.

BEST MODE FOR CARRYING OUT THE INVENTION

Figure 1:
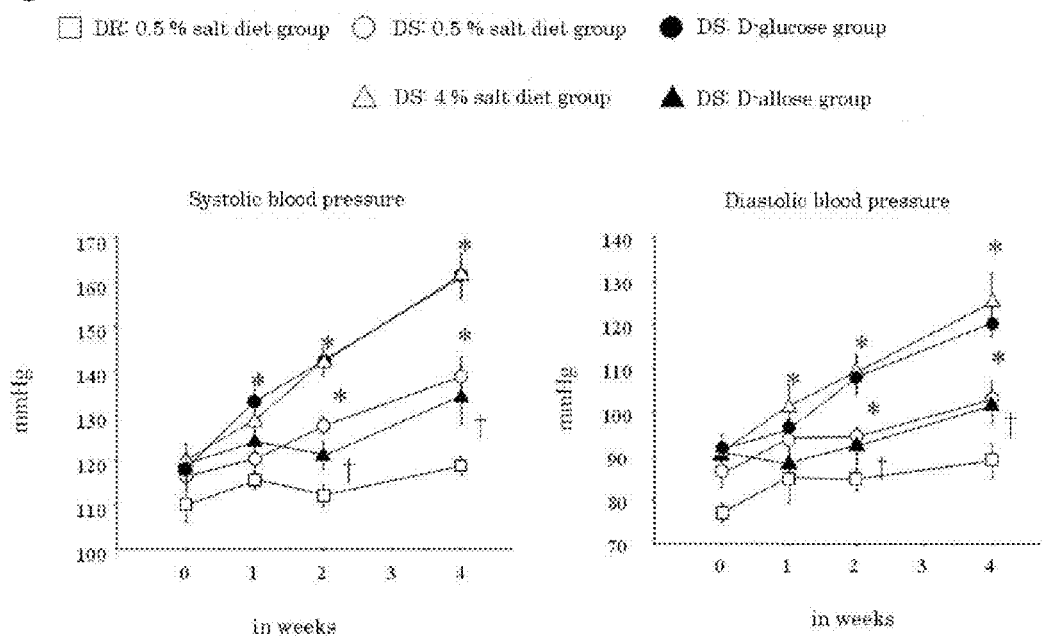
FIG. 1 shows graphs depicting the effect of D-allose on suppressing the increase of blood pressure.

D-Allose is one of rare sugars with various physiological activities having been elucidated by research works so far about rare sugars. Rare sugar can be defined as monosaccharide and sugar alcohol present in a trace amount in the natural kingdom. Monosaccharides existing abundantly in the natural kingdom include seven types, namely D-glucose, D-fructose, D-galactose, D-mannose, D-ribose, D-xylose, and L-arabinose, while monosaccharides excluding them are all rare sugars. Additionally, sugar alcohol is generated by reducing a monosaccharide. Since a relatively large amount of D-sorbitol exists in the natural kingdom but sugar alcohols excluding D-sorbitol exist less quantitatively, therefore, these sugar alcohols are also considered as rare sugar. D-Allose (D-allohexose) as a subject to be separated and recovered in accordance with the invention is the D form of allose classified in aldose (aldo-hexose), with the melting point of 178° C., which is a hexose ($C_6H_{12}O_6$).

The process of producing D-allose includes a process comprising reducing D-allonic acid lactone with sodium amalgam, and the process of synthetically preparing D-allose from D-psicose using L-rhamnose isomerase, as described in Shaquatt Whein Piya, et al, Journal of Fermentation and Bioengineering, Vol. 85, pp. 539-541 (1993). Additionally, a process of generating D-allose from D-psicose by reacting a solution containing D-psicose with D-xylose isomerase, is described in JP-A-2002-17392. For generating D-allose according to the process described in the publication, D-allose is recovered as an enzyme reaction solution containing freshly generated D-allose together with unreactive D-psicose. More recently, the enzyme for use in converting a substrate capable of being converted to D-allose to D-allose is L-rhamnose isomerase derived from *Pseudomonas stutzerii* LL172 (IPOD FERM BP-08593) described in WO 2004/063369 or *Bacillus pallidus* strain 14a (IPOD FERM AP-20172) described in the Japanese Patent Application 2005-95538, as an enzyme capable of generating D-allose from D-psicose.

For example, D-allose can be obtained efficiently as a solution containing D-allose, by subjecting a solution containing a substrate as a raw material to an enzyme reaction using a protein with the L-rhamnose isomerase activity derived from *Bacillus pallidus* strain 14a (IPOD FERM AP-20172) at 60° C. to 80° C. From the solution containing D-allose, further, D-allose can be separated and recovered, while D-allose can be produced continuously by the reaction.

As the D-allose, D-allose and/or a derivative thereof may be used. D-Allose is a stably available raw material of monosaccharides. Because D-allose is a monosaccharide derived naturally and is widely used as a food or for use in foods, it can be said that D-allose is highly safe for humans.

The derivative of D-allose is now described. Compounds prepared by modifying the molecular structure of a certain starting compound with a chemical reaction are referred to as derivatives of the starting compound. Derivatives of hexoses including D-allose are generally sugar alcohols (Via the reduction of monosaccharides, the aldehyde groups or ketone groups therein are modified to alcohol groups, so that the resulting products are generally polyhydric alcohols with the number of the hydroxyl groups therein being equal to the number of the carbon atoms), uronic acids (from the oxidation of the alcohol groups in monosaccharides; known naturally occurring uronic acids are D-glucuronic acid, galacturonic acid, and mannuronic acid), and aminosugars (including glucosamine, chondrosamine and glucosides, as prepared by substituting the OH group in a sugar molecule with NH2 group). However, the derivatives thereof are not limited to them.

The invention relates to food additives, food materials, foods and drinks, health foods and drinks, pharmaceutical products and feeds, for use in preventing and therapeutically treating hypertension, of which the symptoms can be ameliorated through the suppression of the increase of blood pressure or of which the onset can be prevented, or for use in preventing and therapeutically treating cardiovascular disorders such as hypercardia, as the effect of suppressing the onset of hypertension.

The food additives, the food materials, the foods and drinks, the health foods and drinks, the pharmaceutical products and the feeds in accordance with the invention contain D-allose and/or a derivative thereof and/or a mixture thereof as the active ingredient.

Specifically, D-allose can be used as a composition in blend with D-allose and/or a derivative thereof as the active ingredient. The composition can be orally given by oral administration or can be applied dermally and the like. According to general methods, the composition can be blended in oral or parenteral products for use in various fields including food additives, food materials, foods and drinks, health foods and drinks, external dermal agents, pharmaceutical products and feeds. The effect thereof on suppressing the onset of hypertension is promising in practically advantageous applications in health foods and drinks, and nutritional foods and drinks and additionally in pharmaceutical fields, food additives, food materials, foods and drinks, feeds and cosmetic fields. The biological application of D-allose includes the use thereof in foods and drinks, pharmaceutical products, fertilizers, feeds and external dermal agents, so that the effect thereof on suppressing the onset of hypertension and various secondary effects (the effect on suppressing the onset of cardiovascular disorders such as hypercardia and the like) can be obtained.

D-Allose and/or a derivative thereof is blended to a content of 0.1 to 50% by weight in the composition.

Active utilization of the functions of D-allose and/or a derivative thereof in accordance with the invention enabled the development of health foods and drink, foods as nutritional foods and drinks for patients and additionally the development of feeds for feeding animals such as cattle, chicken and fish. In case that D-allose is used by actively utilizing the functions thereof, the content is appropriately adjusted in a manner depending on the level of the intended functions, the mode for using the composition, and the amount of the composition to be used, but is not limited in any specific way. The content is for example 0.1 to 50% by weight.

The inventors demonstrated experimentally that D-allose had an effect of suppressing the onset of hypertension.

Therefore, a hypertensive disease with no distinct etiology, namely essential hypertension occupying 90% or more of hypertensive diseases is now described below. A great number of research works and development have been done so far about the etiology of hypertensive diseases as adult diseases, particularly the etiology of essential hypertension (hypertension without any other essential diseases). It has been elucidated that complicated blood pressure regulation mechanisms are combined together to establish hypertensive diseases. Such factors include renal pressor factors, adrenal cortex, neurofactors and neuro-/nervous body fluid factors, blood circulation factors, and factors involved in the sodium metabolism.

As to the renal pressor factors, renin is a proteinase generated in the juxtaglomerular cells and is released in a manner depending on the inner pressure change in the juxtaglomerular apparatus, which works to specifically hydrolyze the Leu-10-Leu-11 bond (Leu-Val in humans) in angiotensinogen as a substrate in the $\alpha 2$ globulin to generate angiotensin I (decapeptide). This loses two amino acids therein due to the action of the angiotensin I transferase, to be modified as angiotensin II (octapeptide). Angiotensin II directly constricts the smooth muscle in peripheral vascular tubes, so that a strong pressor activity and action can be exerted. As to adrenal cortex, angiotensin II acts on the spherical layer of adrenal cortex, raising the secretion of aldosterone distinctly. The pressor action of the renin-angiotensin system is therefore believed to function via aldosterone (generally, hypertension involving the abnormal activation of the renin-angiotensin system includes renovascular hypertension, malignant hypertension, and hypertension due to renin-generating tumor in a rare case; it is said that the renin-angiotensin system is also involved in essential hypertension). For the neurofactors and neuro-/nervous body fluid factors, it is suggested that the sympathetic nerve system may be involved in these factors (however, no definite verification has been obtained yet). The blood circulation factors are derived from the vascularly reactive mechanism or the systolic mechanism of vascular tube smooth muscle. Besides, genetic factors and factors in relation with the sodium metabolism are also included.

For use in the therapeutic treatment of such hypertensive diseases, hypotensive agents are widely used. The agents lower blood pressure by exerting the influence on the blood pressure regulation mechanisms. A great number of drugs with different action mechanisms exist. As such, for example, there are used (1) pharmaceutical drugs causing vasodilatation by directly acting on vascular tube smooth muscle, (2) pharmaceutical drugs suppressing the activities of the sympathetic nerve at a certain point in the pathway from the central nerve system to peripheral vascular tube receptors (central sympathetic nerve-suppressing drugs, pharmaceutical drugs suppressing both the central nerve system and peripheral nerves, ganglionic blocking agents, adrenergic neuron blockers, $\alpha$-receptor blockers), (3) diuretics, and (4) angiotensin antagonists (drugs blocking the action of angiotensin II, angiotensin I transferase-suppressing drugs).

However, all these pharmaceutical drugs are used as therapeutic agents for hypertensive patients and also require accurate prescriptions prepared by doctors based on appropriate diagnosis. Therefore, it is desirable to prevent hypertension by dietary therapy and the like, with no use of such therapeutic agents. Therefore, subsequent research works from the respect of preventive medicine have verified that hypertension can be prevented or suppressed by controlling the salt intake.

Specifically, it is demonstrated that excess intake of salt (sodium chloride) seriously influences the blood pressure regulation mechanisms involved in the etiology of hypertension, so that hypertension occurs. In such circumstances, instructions including salt regulation have been done for a hypertensive disease with no distinct etiology, namely essential hypertension occupying 90% or more of hypertensive diseases.

Based on the results of research works on hypertensive diseases, the medical societies recommend the reduction of dietary sodium intake in almost all individuals. For example, the regulation of sodium intake to 3.0 g per adult per day is recommended (The American Cardiology Association, Diet Guidelines for Healthy American Adults, Circulation 77: 721-724, 1988). Similarly, it is shown by research works using DASH that the reduction of sodium intake to 1.5 g decreased blood pressure more than a diet with 2.4 g salt did. (NIH News Release, May 17, 2000 "NHLBI study shows a significant advantage of dietary sodium reduction on blood pressure").

Generally, people know that the reduction of sodium intake is advantageous. However, many people would never reduce sodium intake or cannot reduce sodium intake. Sodium action is significant, particularly in salt-sensitive individuals. Therefore, such individuals are with a high risk of the affliction with hypertension. Hypertension in salt-sensitive individuals is a pathological symptom to be discriminated from hypertensive diseases of other types, in that the hypertension is caused by sodium chloride as a common dietary component. When such hypertension is left without any therapeutic treatment, the incidence rates of myocardial infarction, stroke, heart failure, renal function disorders, organ disorders and other cardiovascular symptoms in patients afflicted with the symptoms thereof would increase.

Further, the inventors verified experimentally that D-allose not only suppressed the increase of blood pressure but also suppressed hypercardia (at a certain level) occurring as the consequence thereof.

It is reported from non-clinical tests and clinical tests that hypertension increases loads in heart, causing hypercardia [Schmieder R E, et al., Cardiovasc Pharmacol., 16 (Suppl. 6), S16-S22 (1990); Chevalier B, et al., Circulation, 92, pp. 1947-1953 (1995)]. It can be said that hypercardia is a compensation mechanism to maintain cardiac output in countermeasure to hypertension. When hypertension is sustained for a long term, however, abnormalities in coronary circulation regulations, such as the increase of coronary vascular tube resistance, the reduction of the preliminary capacity of coronary circulation, and the elevation of the lower limit of the coronary circulation automatic regulation, are triggered, so that the compensating mechanism reaches the limit, causing gradually the reduction of cardiac constriction potency and leading to cardiovascular diseases such as ischemic cardiac diseases and heart failure [Marcus M L, et al., Circulation, 75 (Suppl. 1), I19-I25 (1987)].

Hypercardia means the state of heart in an abnormally larger size than general, due to genetic background or acquired pressure loading, leading to a possibility of heart failure. Nonetheless, no pharmaceutical agent suppressing hypercardia for preventing the progress of hypercardia or promoting the retraction thereof has been commercially available currently. This is due to the strong adverse actions of the currently known pharmaceutical agents suppressing hypercardia so that the pharmaceutical agents are never applicable to humans in a practical sense. Therefore, a pharmaceutical agent suppressing or ameliorating hypercardia without any problem such as adverse actions is strongly desired. It can be said that D-allose is an anti-hypertensive agent (including hypotensive agents and pharmaceutical agents suppressing hypercardia) capable of overcoming such problems.

Additionally, the anti-hypertensive agent for use in accordance with the invention is mainly formulated as an oral agent, such as tablets, capsules, powders, granules, tablets, fluids, or gel forms. Similarly, the food additives in accordance with the invention may satisfactorily be added in forms of powders, granules, tablets, fluids or gels to foods (including foods and drinks). Furthermore, the food additives may be preliminarily coated with sustained-release agents so as to appropriately exert the action in bodies (in small intestine).

Further, the tablets and the capsules as the oral agents of the anti-hypertensive agent for use in accordance with the invention may preferably contain a single dose and contains for example common excipients as binders such as syrup, acacia or sorbitol, for example fillers such as lactose, sugar or cornstarch.

Additionally, the oral fluid preparation is formed into suspensions, solutions, emulsions, syrups or elixir containing water and oil. The oral fluid formulation may be formulated as a dry product, which can be back to a fluid before use, by adding water or other appropriate excipients to the dry product. For preparing such oral fluid preparation, for example, suspending agents such as sorbitol, syrups or gelatin, emulsifying agents such as acacia and lecithin, non-aqueous excipients such as coconut oil and oily esters (propylene glycol, etc.), and other common pharmaceutical agents including preservatives, additives and seasonings, colorants or vitamins if necessary, may be used. The amount of the chitosan to be added (or the dose thereof) in the food additives or the anti-hypertensive agents in accordance with the invention varies depending on the severity of hypertension, and the body weight, age and sex, and the like. Preferably, the amount thereof is appropriately determined for each patient for use. Generally, a range of 5 to 6 g/day is approximately the standard for therapeutically treating the hypertension of a hypertensive male adult patient of 70 kg, when the daily salt intake is routinely 12 g.

For using the pharmaceutical agent of the invention as a pharmaceutical product, flavonoid at an amount effective for the prevention and therapeutic treatment is preferably formulated together with a pharmaceutically acceptable carrier or diluent. Besides, binders, absorption-promoting agents, lubricants, emulsifying agents, surfactants, anti-oxidants, preservatives, colorants, flavor and sweeteners may be added.

The ratio of the active ingredient flavonoid to the carrier component in such pharmaceutical preparation is within a range of 0.1 to 10% by weight, particularly preferably within a range of 0.5 to 1.0% by weight.

The dosage form thereof as a pharmaceutical preparation includes granules, fine granules, tablets, pills, capsules, aerosols, solutions, suspensions, ointments, gels, pastes and creams. The dosing route thereof includes various dosing routes such as oral route, intravenous route, intra-muscular route, subcutaneous route, and intra-joint cavity route. Additionally, the dose of the active ingredient and the dosing frequency thereof appropriately vary, depending on the symptoms, the age and sex, the dosing route and the like.

The flavonoid of the invention may satisfactorily be added to functional foods. The functional foods mean natural products or processed products thereof containing at least one nutrient. The flavonoid may be applicable to any foods and drinks, for example confectioneries and refreshing drinks.

The details of the invention are now described below. The invention is never limited to these Examples.

EXAMPLE 1

Salt-sensitive Dahl rats with the onset of hypertension were used to investigate the course of the elevation of blood pressure after the start of salt loading as well as to investigate the influence of oral D-allose administration on the generation of active oxygen in vascular tube.

[Method]
(Animals and Treatments)

Salt-sensitive male Dahl rats of age 7 weeks and with the onset of hypertension (DS) and salt-insensitive male Dahl rats of the same age (DR) were used. The DS rats were fed with a 0.5% salt diet or a 4% salt diet (Oriental Yeast Co., Ltd.) for 4 weeks (individually referred to as 0.5% salt diet group and 4% salt diet group). During the period, D-allose or D-glucose was orally given to the 4% salt diet group at 2 g daily/kg body weight (D-allose group or D-glucose group). The DR rats were fed with the 0.5% salt diet group and used as a normal control group. Blood pressure was measured by the tail-cuff method over time, while before salt loading and on the completion of salt loading, urine was collected for one day. On the last day of the observation period, the thoracic aorta was resected. A part thereof was used to quantify the amount of generated active oxygen in the aorta by the lucigenin method, while another part thereof was used to compare the amount of generated active oxygen between the groups by the dihydroxyethidium (DHE) fluorescence method. So as to assay the expression level of the messenger RNA of the NADPH oxidase involved in the increase of tissue oxidative stress (J Hypertens. 2004; 22:2161-2168), further, the renal cortex and the thoracic aorta were partially stored at −80° C.

<Assay of Generated Active Oxygen in Aorta>

The thoracic aorta in pieces was incubated in a buffer containing 10 mmol/L diethyldithiocarbamate supplemented with 118.3 mmol/L NaCl, 4.7 mmol/L KCl, 2.5 mmol/L $CaCl_2$, 1.2 mmol/L $KH_2PO_4$, 1.2 mmol/L $MgSO_4$, 25.0 mmol/L $NaHCO_3$, 5.5 mmol/L glucose, and 0.026 mmol/L EDTA, in oxygen gas streams containing 5% $CO_2$, at 37° C. for 30 minutes, and then transferred to a Krebs-HEPES buffer containing 10 μmol/L lucigenin supplemented with 119 mmol/L NaCl, 20 mmol/L HEPES, 4.6 mmol/L KCl, 1.2 mmol/L $CaCl_2$, 0.4 mmol/L $KH_2PO_4$, 1.0 mmol/L $MgSO_4$, 0.15 mmol/L $Na_2HPO_4$, 25.0 mmol/L $NaHCO_3$ and 5.5 mmol/L glucose, pH 7.4. Then, the luminescence was counted with a luminescence reader (BLR-301; Aloka).

Additionally, a part of the thoracic aorta in pieces was incubated in a Krebs-HEPES buffer containing 10 μmol/L DHE, at 37° C. for 30 minutes, and immediately then, the part was embedded in OCT. A 10-μm ring slice piece was prepared from the embedded aorta with a cryostat, to observe the intra-tissue localization of ethidium generated from the specific reaction between active oxygen and DHE, along with the intensity of the luminescence, with a co-focus microscope (Bio-Rad).

[Results]

1) Blood Pressure (FIG. 1)

After starting the feeding with the 4% salt diet, the systolic and diastolic blood pressure in the DS rats without any treatment were gradually increased, so that in 4 weeks, the systolic pressure and diastolic pressure were 161±5 mmHg and 125±6 mmHg, respectively. In the D-allose group, the systolic pressure and diastolic pressure were retained at 135±7 mmHg and 102±4 mmHg, respectively. No significant difference from the DS rats fed with the 0.5% salt diet was observed in the D-allose group. In the D-glucose group, the systolic pressure and diastolic pressure were 162±5 mmHg and 125±6 mmHg, respectively. The increase of blood pressure at the same level as in the 4% salt diet group without any treatment was observed.

2) Body Weight and Organ Weight (Table 1)

No significant change in body weight in the non-treated DS rats was observed between the 0.5% salt diet and the 4% salt diet fed for 4 weeks. In the D-allose group compared with the non-treated group with the 0.5% salt diet or the group with the 4% salt diet, the increment of the body weight was reduced, but with no significant difference from the D-glucose group. Additionally, no difference in feed intake was observed among the three groups fed with the 4% salt diet (the non-treated group; 20.4±1.0 g/day/rat: the D-allose group; 20.6±0.8 g/day/rat: the D-glucose group; 21.4±0.8 g/day/rat). The ratio of heart weight to body weight was increased with the 4% salt diet, while the ratio was significantly suppressed in the D-allose group. The ratio of kidney weight to body weight was increased with the 4% salt diet, with no influence of the treatment with D-allose or D-glucose.

3) Urine Generation and Protein Excretion in Urine (Table 1)

The urine volume and the sodium excretion in urine were significantly increased with the 4% salt diet. In the individual groups namely the 4% salt diet group without any treatment, the D-allose group and the D-glucose group, no significant difference was observed. The protein excretion in urine was increased in the 4% salt diet group without any treatment, while the protein excretion in urine was apparently suppressed in the D-allose group, with no change in the D-glucose group.

TABLE 1

| | | DS rats | | | |
|---|---|---|---|---|---|
| | DR rats (n = 5) | 0.5% salt diet group (n = 6) | 4% salt diet group (n = 6) | D-allose group (n = 6) | D-glucose group (n = 6) |
| Before salt loading | | | | | |
| Body weight (g) | 208 ± 4 | 235 ± 5 | 230 ± 3 | 228 ± 3 | 235 ± 4 |
| Urine volume (ml/day) | 9.7 ± 0.4 | 11.3 ± 0.4 | 9.3 ± 1.5 | 7.8 ± 1.0 | 9.0 ± 1.9 |
| Na excretion in urine (mEq/day) | 13 ± 1 | 13 ± 3 | 11 ± 1 | 12 ± 2 | 10 ± 1 |
| Protein excretion in urine (mg/day) | 5.4 ± 1.2 | 9.1 ± 3.2 | 13.0 ± 4.0 | 9.5 ± 1.2 | 13.1 ± 3.2 |
| After 4-week feeding | | | | | |
| Body weight (g) | 318 ± 6 | 377 ± 8 | 369 ± 7 | 345 ± 7*# | 356 ± 10 |
| Urine volume (ml/day) | 10.8 ± 1.0 | 9.4 ± 0.9 | 30.5 ± 2.7* | 28.7 ± 2.2* | 32.0 ± 2.9* |
| Na excretion in urine (mEq/day) | 16 ± 1 | 13 ± 1 | 115 ± 7* | 126 ± 6*# | 123 ± 7* |
| Protein excretion in urine (mg/day) | 13.9 ± 1.8 | 18.2 ± 6.3 | 81.8 ± 16.5* | 31.3 ± 11.8*# | 85.3 ± 20.5* |
| Heart weight (mg) | 830 ± 12 | 960 ± 14 | 1121 ± 27* | 994 ± 28*# | 1066 ± 35* |
| Kidney weight (mg) | 1089 ± 7.8 | 1266 ± 23 | 1472 ± 47* | 1389 ± 25* | 1370 ± 36* |

TABLE 1-continued

|  | DR rats (n = 5) | DS rats | | | |
|---|---|---|---|---|---|
|  |  | 0.5% salt diet group (n = 6) | 4% salt diet group (n = 6) | D-allose group (n = 6) | D-glucose group (n = 6) |
| Heart/body weight ratio ($\times 10^{-3}$) | 2.61 ± 0.03 | 2.55 ± 0.04 | 3.04 ± 0.04* | 2.88 ± 0.07*# | 3.00 ± 0.08* |
| Kidney/body weight ratio ($\times 10^{-3}$) | 3.42 ± 0.07 | 3.35 ± 0.05 | 3.99 ± 0.07* | 4.03 ± 0.03* | 3.85 ± 0.07* |

*$p < 0.05$ vs DS: 0.5 salt diet group,
$p < 0.05$ vs DS: 4% salt diet group

Figure 2A:
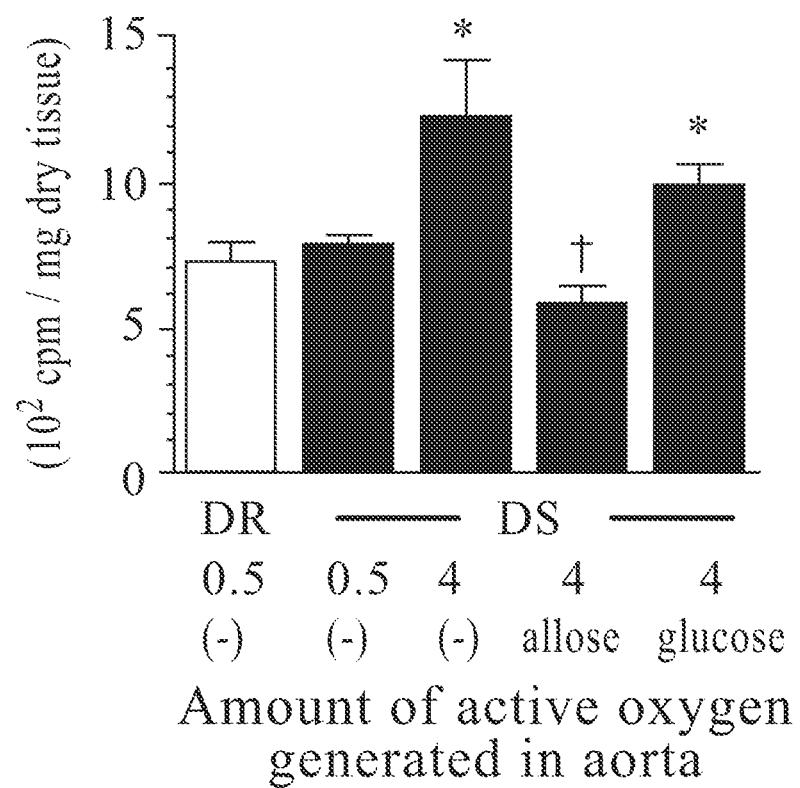
FIGS. 2a and 2b show photographs and bar graphs depicting the effect of D-allose on suppressing the generation of active oxygen in aorta.
Figure 2B:
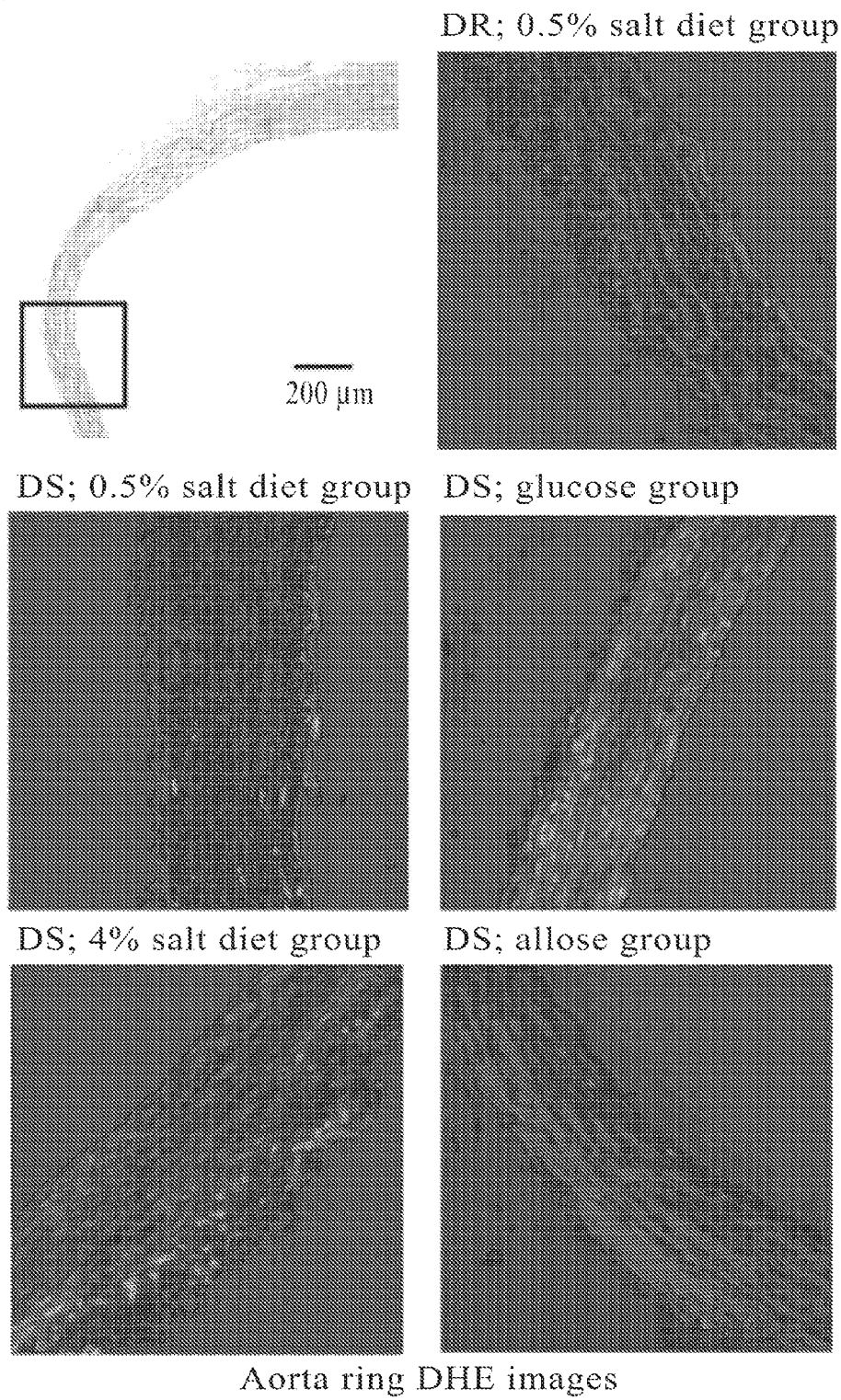

4) Generation of active oxygen in aorta (FIGS. 2a and 2b)

According to the assay of the generated active oxygen in the rat thoracic aorta by the lucigenin method, a significant increase in the active oxygen generation was observed in the 4% salt diet group without any treatment, while in the D-allose group, the active oxygen generation was suppressed to the level as observed in the 0.5% salt diet group or the DR normal control group. Alternatively, no such suppressive effect was observed from the D-glucose treatment. On the DHE fluorescence images, the enhancement of signal accumulation was observed in the aorta media nucleus obtained from the 4% salt diet group without any treatment, which was suppressed in the D-allose group but which never changed in the D-glucose group.

5) Messenger RNAs of NADPH Oxidase-Composing Factors (Table 2)

The levels of the messenger RNAs of p22phox and Nox analogs (Nox-1, gp91phox, Nox-4) as the NADPH oxidase-composing factors were assayed and compared in between thoracic aorta and renal cortex. The messenger RNAs of gp91phox and Nox-4 in the thoracic aorta in the 4% salt diet group without any treatment and that of gp91phox in the renal cortex were significantly increased individually, while both of them were suppressed via the combined administration of D-allose to the level observed in the 0.5% salt diet group or in the DR normal control group.

TABLE 2

|  | DR rats | DS rats | | | |
|---|---|---|---|---|---|
|  |  | 0.5% salt diet group | 4% salt diet group | D-allose group | D-glucose group |
| Aorta |  |  |  |  |  |
| $p22^{phox}$ | 1.00 ± 0.05 | 0.95 ± 0.25 | 1.35 ± 0.50 | 0.83 ± 0.21 | 1.14 ± 0.32 |
| $gp91^{phox}$ | 1.00 ± 0.18 | 1.23 ± 0.15 | 3.02 ± 0.88* | 1.34 ± 0.27# | 1.90 ± 0.19* |
| Nox1 | 1.00 ± 0.05 | 1.11 ± 0.04 | 1.18 ± 0.24 | 0.74 ± 0.22 | 0.85 ± 0.24 |
| Nox4 | 1.00 ± 0.10 | 0.94 ± 0.09 | 2.15 ± 0.51* | 1.36 ± 0.10*# | 1.75 ± 0.24* |
| Renal cortex |  |  |  |  |  |
| $p22^{phox}$ | 1.00 ± 0.12 | 1.19 ± 0.07 | 1.23 ± 0.14 | 1.18 ± 0.20 | 1.19 ± 0.06 |
| $gp91^{Phox}$ | 1.00 ± 0.15 | 0.96 ± 0.10 | 1.55 ± 0.16* | 0.97 ± 0.15# | 1.20 ± 0.28 |
| Nox1 | 1.00 ± 0.07 | 0.92 ± 0.16 | 0.84 ± 0.13 | 0.88 ± 0.11 | 1.03 ± 0.24 |
| Nox4 | 1.00 ± 0.15 | 1.28 ± 0.14 | 1.27 ± 0.26 | 1.32 ± 0.22 | 1.38 ± 0.16 |

*$p < 0.05$ vs DS: the 0.5% salt diet group,
$p < 0.05$ vs DS: the 4% salt diet group

[Discussion]

The mechanism of the blood pressure elevation caused by salt loading has still included unknown features, but animal experiments have approximately elucidated that the increase of the oxidative stress in cardiovascular tissues leads to the elevation of blood pressure (*Curr Hypertens Rep;* 2: 98-105). It has been known additionally that salt-sensitive hypertension has a close relation with insulin resistance. In a past report, it is described that the amelioration of insulin resistance by a therapeutic treatment with an active oxygen-eliminating agent can be expected (*Am J Hypertens* 1998; 11: 397-402.; *Hypertension* 2002; 40: 83-89).

Zhang et al. report that salt loading on a DS rat fed with a high-calories diet additionally enhanced the level of the blood pressure increase, suggesting a close relation between the calories intake and the salt-sensitive hypertension (*Am J Hypertens* 1999; 12: 183-187). Hypertension and obesity as risk factors of cardiovascular diseases largely depend on the individual dietary lifestyles and habits. The American Heart Association recommends that the excess intake of calories sources should be prevented daily and exercise habits should be acquired (AHA Dietary Guidelines. Revision 2000: A statement for healthcare professionals from the nutrition committee of the American Heart Association. *Circulation* 2000; 102: 2284-2299). In this sense, 1) D-allose is a non-calories monosaccharide and the use of D-allose as a sweetener in foods leads to the suppression of the excess calories intake, to help the increase of body weight directly leading to hypertension. Furthermore, 2) because D-allose has an action to suppress the generation of active oxygen, D-allose has an additional value in ameliorating insulin resistance and reducing oxidative stress as a cause of tissue disorders following hypertension.

The effect of D-allose on suppressing the increase of blood pressure in salt-sensitive rats with the onset of hypertension as demonstrated in the results of the test may mainly be due to the reduction of oxidative stress in vascular tissues as described above in 2). The use of D-allose as an alternative enables the control of total calories intake, so that D-allose exerts a synergistic effect on the suppression of the progress in salt-sensitive hypertension because of the reason of above in 1). Furthermore, it is reported that D-allose modifies the glucose transporter functions in a manner depending on the tissue. Accordingly, the influence of D-allose on sugar intake into tissues may work as a mechanism to suppress the salt sensitivity of blood pressure.

EXAMPLE 2

Using a spontaneously hypertensive rat, the influence of oral D-allose administration on the course of the increase of blood pressure under salt loading or no salt loading was examined.

[Method]
<Animals and Treatments>

Male spontaneously hypertensive rats of age 8 weeks (SHR) and male Wister KYOTO rats (WKY) of the same age were used. SHR was fed with a 0.5% salt diet or a 8% salt diet (Oriental Yeast Co., Ltd.) for 4 weeks (individually referred to as the 0.5% salt diet group and the 8% salt diet group). Additionally, D-allose or D-glucose was orally given to the 0.5% salt diet group and the 8% salt diet group, at 2 g daily/kg body weight (D-allose group or D-glucose group) during the period. WKY was fed with the 0.5% salt diet and used as a normal control group. Systolic blood pressure was measured by the tail-cuff method over time.

[Results]

Figure 3:
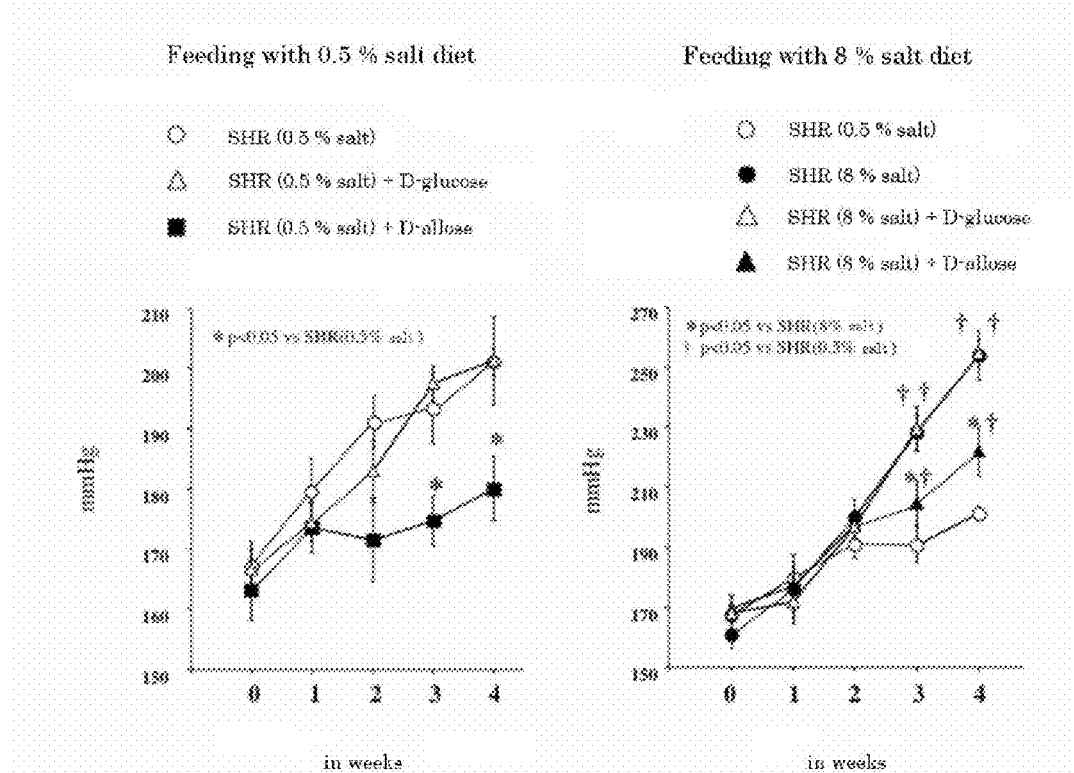
FIG. 3 shows graphs depicting the effect of D-allose on the blood pressure during the SHR-induced systolic stage.

1) Blood Pressure (FIG. 3)

In SHR, the systolic blood pressure was elevated from 169±4 mmHg to 201±2 mmHg during the 4-week period of feeding with the 0.5% salt diet, while the change of the systolic pressure in WKY was from 124±4 mmHg to 131±4 mmHg. In SHR, the increase of the blood pressure after feeding with the 8% salt diet significantly elevated the increase of the blood pressure. In 4 weeks, the systolic blood pressure reached 254±8 mmHg. Via the treatment with D-allose, the increase of the blood pressure by feeding with the 0.5% salt diet was significantly suppressed. The systolic blood pressure was 180±5 mmHg. Via the treatment with D-allose, the increase of the blood pressure by feeding with the 8% salt diet remained 222±8 mmHg. Alternatively, the increase of the systolic blood pressure in the D-glucose groups by feeding with any of the salt diets was observed at the same level as in the non-treatment control. (0.5% salt diet+D-glucose: 201±7 mmHg; 8% salt diet+D-glucose: 255±5 mmHg).

2) Heart Weight and Kidney Weight (Table 3)

No significant change in body weight was observed in SHR between the 0.5% salt diet group and the 8% salt diet group. Compared with the control, the heart weight and the heart/body weight ratio were significantly suppressed in the D-allose groups fed with the 0.5% salt diet and the 8% salt diet. Meanwhile, the heart weight and the heart/body weight ratio in the D-glucose groups fed with any of the salt diets were not different from those in the control.

Industrial Applicability

When the effect of D-allose on suppressing the onset of hypertension is established, D-allose may possibly be utilized in forms of foods and nonessential grocery items, not as a pharmaceutical agent, by actively using the fact that D-allose is a sugar, unlike pharmaceutical agents so far. It is needless to say that D-allose can be used as a pharmaceutical agent for suppressing the onset of hypertension. Additionally, D-allose may have higher social effects (including economic effects) when D-allose is used in forms of foods and nonessential grocery items.

D-allose may become an excellent food additive or antihypertensive agent, in that D-allose never requires the regulation or control of salt intake; that D-allose can be used in seasoning meals in the same manner as for healthy humans (animals) by actively utilizing the definite feature that D-allose is a sugar; and that salt giving salty taste (salty taste is tasted as a general taste of Na+ and Cl− as edible salt) can be used with no requirement of actively preparing low-salt diets and therefore, the resulting meals may never be very dull and dreary low-salt diets.

Furthermore when it is established that D-allose not only suppresses the increase of blood pressure but also has an effect of suppressing hypercardia occurring as the consequence thereof to a certain level, D-allose may be a pharmaceutical agent for suppressing or ameliorating hypercardia with no problematic adverse effects. The effect thereof of suppressing hypercardia may be used in forms of foods and nonessential grocery items.

The invention claimed is:

1. A method for suppressing an increase of blood pressure, comprising:
    administering a compound consisting of D-allose to a subject in need of suppressing the increase of blood pressure,

TABLE 3

| | Weight before treatment (g) | Weight after 4 weeks (g) | Heart weight (mg) | Kidney weight (mg) | Heart/body weight ratio (×10⁻³) | Kidney/body weight ratio (×10⁻³) |
|---|---|---|---|---|---|---|
| WKY | 298 ± 5 | 355 ± 7 | 993 ± 20 | 1073 ± 3 | 2.80 ± 0.08 | 3.02 ± 0.02 |
| SHR | | | | | | |
| 0.5% salt diet group | | | | | | |
| Control | 239 ± 6 | 291 ± 7 | 1134 ± 38 | 1192 ± 45 | 3.89 ± 0.08 | 4.17 ± 0.07 |
| D-glucose groups | 243 ± 8 | 301 ± 4 | 1180 ± 35 | 1206 ± 32 | 3.92 ± 0.15 | 3.02 ± 0.02 |
| D-allose groups | 239 ± 5 | 292 ± 4 | 1042 ± 23* | 1212 ± 34 | 3.56 ± 0.05* | 4.15 ± 0.08 |
| 8% salt diet group | | | | | | |
| Control | 253 ± 4 | 308 ± 4 | 1468 ± 16# | 1371 ± 44# | 4.69 ± 0.08# | 4.38 ± 0.17# |
| D-glucose groups | 253 ± 2 | 306 ± 5 | 1437 ± 38 | 1342 ± 41 | 4.70 ± 0.13 | 4.40 ± 0.19 |
| D-allose groups | 252 ± 5 | 304 ± 6 | 1337 ± 50* | 1387 ± 61 | 4.40 ± 0.06* | 4.57 ± 0.17 |

*p < 0.05 vs SHR: the 0.5% or the 8% salt diet group control,
p < 0.05 vs SHR: the 0.5% salt diet group control

[Discussion]

It was indicated that the oral administration of D-allose effectively suppressed the increase of the systolic blood pressure in the spontaneously hypertensive rats (SHR). Under loads with high levels of salt, the increase of blood pressure was more significant. D-Allose could suppress the increase. Additionally, the administration of D-allose suppressed hypercardia as a cause of heart diseases. Hypercardia progresses under loads of high levels of salts in the same manner. However, D-allose suppressed the progress.

wherein the compound consisting of D-allose is therapeutically effective to suppress the increase of blood pressure.

2. The method according to claim 1, wherein the compound consisting of D-allose is administered in a form of a composition comprising the compound consisting of D-allose.

3. The method according to claim 2, wherein the composition is in a form selected from the group consisting of food additives, food materials, foods and drinks, health foods and drinks, pharmaceutical products and feeds.

4. The method according to claim 3, wherein the composition comprises the compound consisting of D-allose as an active ingredient for the prevention and therapeutic treatment of the onset of hypertension and/or the onset of cardiovascular diseases which comprise hypercardia.

5. The method according to claim 3, wherein the composition comprises the compound consisting of D-allose in an amount of 0.1 to 50% by weight in the composition.

6. The method according to claim 1, wherein said administration suppresses the increase of blood pressure which is caused due to salt-sensitive hypertension.

* * * * *

UNITED STATES PATENT AND TRADEMARK OFFICE
CERTIFICATE OF CORRECTION

PATENT NO. : 8,440,619 B2  Page 1 of 1
APPLICATION NO. : 12/065452
DATED : May 14, 2013
INVENTOR(S) : Tokuda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1182 days.

Signed and Sealed this
Eighth Day of September, 2015

Michelle K. Lee
*Director of the United States Patent and Trademark Office*